United States Patent [19]

Kalchauer

[11] Patent Number: 5,625,088
[45] Date of Patent: Apr. 29, 1997

[54] PROCESS FOR PREPARING DIMETHYLDICHLOROSILANE

[75] Inventor: Wilfried Kalchauer, Burghausen, Germany

[73] Assignee: Wacker-Chemie GmbH, Munich, Germany

[21] Appl. No.: 668,667

[22] Filed: Jun. 25, 1996

[30] Foreign Application Priority Data

Aug. 17, 1995 [DE] Germany ............... 195 30 292.3

[51] Int. Cl.$^6$ ........................................ C07F 7/16
[52] U.S. Cl. ................................................. 556/473
[58] Field of Search ...................................... 556/473

[56] References Cited

U.S. PATENT DOCUMENTS

| | | | |
|---|---|---|---|
| Re. 33,452 | 11/1990 | Ward, III et al. | |
| 2,478,493 | 8/1949 | Levine | 556/473 |
| 2,710,875 | 6/1955 | Daudt | 556/473 |
| 2,865,939 | 12/1958 | Little et al. | 556/479 |
| 4,973,725 | 11/1990 | Lewis et al. | |
| 5,243,061 | 9/1993 | Webb et al. | 556/473 X |
| 5,306,328 | 4/1994 | Streckel et al. | |

OTHER PUBLICATIONS

"Direct Formation of $(CH_3)_2HSiCl$ from Silicon and $CH_3Cl$" by Margrini et al. J.Phys. Chem. 1989, 93, 5563–5568.

*Primary Examiner*—Paul F. Shaver
*Attorney, Agent, or Firm*—Martin Connaughton

[57] ABSTRACT

A process for preparing dimethyldichlorosilane by reacting chloromethane with silicon in the presence of a catalyst combination comprising the metals or compounds of the metals copper, zinc and tin and/or antimony, and chlorosilanes or chlorodisilanes as activators. The activators are fed into the reactor as a gas containing at most 15% by volume of hydrogen.

6 Claims, No Drawings

PROCESS FOR PREPARING DIMETHYLDICHLOROSILANE

FIELD OF INVENTION

The invention relates to a process for preparing methylchlorosilanes by reacting chloromethane with silicon, with a high selectivity in respect of dimethyldichlorosilane being achieved by passing in activators.

BACKGROUND OF INVENTION

Processes for preparing methylchlorosilanes by reaction of silicon with chloromethane (direct synthesis) in the presence of suitable catalysts and catalyst combinations are already known. U.S. Pat. No. Re. 33,452 describes a direct synthesis process using a catalyst combination of the elements or the compounds of copper, zinc and tin. The ratio of the catalysts copper, zinc and tin to one another has a strong influence on the process, in particular on the productivity and the selectivity, while the form, such as metal, alloys or compounds, in which the catalysts are introduced into the catalyst composition, is of subordinate importance.

A. Magrini et al.; J. Phys. Chem. 93, 1989, 5563, describe the activation by means of a trichlorosilane/chloromethane mixture of surfaces of pure polycrystalline silicon on which copper has been vapor-deposited. In the subsequent reaction with pure chloromethane, a higher selectivity in respect of dimethylchlorosilane, methyldichlorosilane and methyltrichlorosilane is achieved. The proportion of dimethyldichlorosilane decreases.

U.S. Pat. No. 4,973,725 describes a direct synthesis process for selectively preparing organohalohydrosilanes in which the gas fed into the reactor comprises at least 20% by volume of hydrogen and an organohalosilane or organohalohydrosilane as activator.

SUMMARY OF INVENTION

It is an object of the present invention to make available a process for preparing methylchlorosilane by reacting chloromethane with silicon, where, independent of the composition of the catalyst, a relatively high production rate and a relatively high selectivity in respect of dimethyldichlorosilane is obtained.

The invention provides a process for preparing dimethyldichlorosilane by reacting chloromethane with silicon in the presence of a catalyst combination of the metals or compounds of the metals a) copper, b) zinc and c) tin and/or antimony, and activators selected from the group consisting of chlorosilanes of the formula

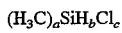 (I), where a and b are, independently of one another, 0, 1, 2 or 3 and c is 1, 2, 3 or 4, and chlorodisilanes of the formula

 (II), where d and e are, independently of one another, 0, 1 or 2, f is 1, 2 or 3 and g, h and i are, independently of one another, 0, 1, 2 or 3, where the activators are added in gaseous form containing at most 15% by volume of hydrogen.

The present invention is based on the recognition that the production rates of dimethyldichlorosilane when using the above catalyst combination in the presence of a small amount of hydrogen can be increased by passing in catalyst activators.

Preferably, the gas fed into the reactor contains at least 0.05% by volume, preferably 0.1% by volume, more preferably 0.5% by volume of activator and at most 5% by volume, in particular 2% by volume, of activator, in each case calculated as gaseous activator.

However, it is also possible to use smaller and larger proportions by volume of activators, with the increase in the production rates of dimethyldichlorosilane being smaller when smaller amounts are used. Higher proportions of activator effect no significant increase in the production rates.

The process is carried out in a fluidized-bed reactor, preferably in the temperature range from 250° to 400° C., more preferably at from 250° to 360° C. The process is carried out at a pressure from that of the surrounding atmosphere (i.e. at about 0.1 MPa) to 0.5 MPa, but it is also possible to use higher pressures.

The process can be carried out using pure chloromethane and activator or mixtures of chloromethane, activator and inert gas; inert gases which can be used are, nitrogen or argon. Preference is given to using no inert gas.

In a preferred embodiment, the amount of the gas stream is selected such that a fluidized bed comprising catalyst composition and gas is formed in the reactor. The mixture of silicon and catalyst is referred to as catalyst composition. Unreacted chloromethane and, optionally, inert gas and the gaseous methylchlorosilanes leave the reactor. The entrained particles may be separated from the gas stream by means of one or more cyclones, with large entrained particles from the catalyst composition being returned to the reactor. The silane is separated from residual amounts of dust and unreacted chloromethane and passed to distillation. Purified, unreacted chloromethane can be fed back into the reactor.

The introduction of the gas stream into the reactor can be carried out in such a way that the chloromethane and the activator are introduced into the reactor via separate lines, or the activator is added in a targeted manner to the chloromethane prior to this being blown into the reactor, or an activator-containing circulating chloromethane is used.

Circulating chloromethane refers to that chloromethane which is blown into the reactor to form the fluidized bed, but is not reacted. Entrained solid impurities and also the products formed in the reaction, such as silanes and hydrocarbons, are separated off and the chloromethane is again introduced into the reactor.

Activators used are compounds which are themselves formed in direct synthesis. This has the advantage that in the distillative work-up of crude silane there is no occurrence of new compounds which would require a change in the column structure or distillation concept, but these compounds are readily available and that the use of partially purified circulating chloromethane is possible. The activators can be used as pure substances or as mixtures of various activators which can contain inert gases such as nitrogen or with hydrocarbons which are formed in the direct synthesis.

The preparation of the catalyst composition is carried out by mixing of the individual components at room temperature. A subsequent thermal treatment of the catalyst composition prior to introduction into the reactor is possible, but is not carried out in the preferred embodiment.

The process can be carried out continuously or batchwise. Continuously means that the amounts of reacted silicon and catalysts carried out with the reaction dust are continuously replaced, preferably as premixed catalyst compositions.

If a fluidized bed is formed in the reactor, the metering in of the activators is most important in the initial phase, since at the beginning the catalysts used are activated and during the production phase sufficient activators are present in the reactor for activation. In reactor forms in which fresh catalyst composition and fresh chloromethane are metered in at one point and are not mixed with reaction mixture which is already undergoing reaction, the metering in of activator during the entire reaction time is advantageous.

In a preferred embodiment of the process of the invention, silicon having a particle size of less than 700 μm and greater than 20 μm, preferably having a particle size of less than 250 mm and greater than 70 μm, is used. The average size of the silicon particles is preferably in the range from 100 to 200 μm, more preferably in the range from 130 to 170 μm. The silicon used usually has a purity of >99%.

In the process of the invention, a) copper is preferably used in the form of copper oxide mixtures, in the form of copper(II) oxide, in the form of CuCl or in the form of $CuCl_2$. In the case of mixed oxides of the formula $CuO_x$, x has a value of from 0.6 to 1, preference is given to a value of at least 0.7. The copper oxides used can have a small proportion of impurities such as iron, lead, zinc, aluminium, titanium, alkali metals or alkaline earth metals or tin. The impurities preferably do not exceed a total of 3% by weight, with the total concentration of lead preferably being at most 0.005% by weight, the total concentration of alkali metals and alkaline earth metals each being at most 0.04% by weight, the total concentration of barium and strontium being at most 0.008% by weight. The copper oxides used preferably have a particle size of less than 25 μm, with the average particle size being in the range from 10 to 0.1 μm, preferably in the range from 7 to 1 μm and more preferably in the range of 5–1 μm. The copper oxides described can be prepared, for example by the process described in U.S. Pat. No. 5,306,328, with the degree of oxidation being set in a targeted manner by means of the drying temperature and the residence time at this temperature.

Preference is given to using from 0.5% to 10% by weight, in particular from 0.7% to 7% by weight, of copper catalyst, based on metallic copper and silicon used; more preference is given to from 1% to 5% by weight.

In the process of the invention, b) zinc is used in the form of metallic zinc, also as alloy with copper, tin and/or antimony, zinc oxide, zinc carbonate or zinc chloride. The zinc used contains less than 0.005% by weight of lead. The total content of alkali metals and alkaline earth metals is at most 0.04% by weight and the total content of barium and strontium is at most 0.008% by weight. The amount of zinc used is preferably from 0.5% to 60% by weight, in particular from 2% to 40% by weight, based on copper; more preference is given to using from 5% to 30% by weight of Zn.

In the process of the invention, antimony and/or tin are preferably used as metals. Preference is given to using only antimony or tin or compounds of antimony or tin. If antimony and/or tin are used as metals, the particle size is at most 150 μm. In a preferred embodiment, antimony or tin powder having a particle size of at most 45 μm is used. The amount of antimony or tin used is preferably from 200 to 8000 ppm, in particular from 300 to 4000 ppm, based on the copper used; particular preference is given to using from 500 to 2500 ppm of antimony and/or tin.

The type of activator used is chosen according to the chemical composition of the zinc catalyst used.

If oxygen-containing zinc compounds such as ZnO or $ZnCO_3$ are used, preference is given to using chlorosilanes having an Si—H bond or an Si—Si bond. Examples of such chlorosilanes are trichlorosilane, methyldichlorosilane, dimethylchlorosilane, 1,1,2,2-tetramethyldichlorosilane, 1,1,2-trimethyltrichlorodisilane and 1,2-dimethyltetrachlorodisilane. More preference is given to chlorosilanes having an Si—H bond and at least two Si—Cl bonds, for example methyldichlorosilane.

If metallic zinc, zinc alloys or zinc chloride is used as catalyst, preference is given to using silanes having at least two Si—Cl bonds. Examples of such silanes are trichlorosilane, methyldichlorosilane, methyltrichlorosilane, tetrachlorosilane, dimethyldichlorosilane, 1,1,2-trichlorotrimethyldisilane, 1,1,2,2-tetrachlorodimethyldisilane and 1,1-dichlorotetramethyldisilane.

Preference is given to using methyltrichlorosilane, methyldichlorosilane and dimethyldichlorosilane.

The gas fed into the reactor preferably contains at most 10% by volume, in particular at most 5% by volume, of hydrogen, since this only requires additional reactor volume and can adversely affect the selectivity in respect of dimethyldichlorosilane. High concentrations of hydrogen also favor the sintering of the catalysts and lead to deactivation.

EXAMPLES

The results in reactions of silicon with chloromethane in the presence of suitable catalysts depend not only on the makeup and the preparation of the catalyst compositions and on the activators used, but also on the configuration of the experimental plant and the experimental procedure. To eliminate the latter two parameters and to be able to clearly indicate the advantages of the present invention, all experiments presented in the examples were carried out according to the following standardized procedure.

Silicon:
  Granules from Lilleby Smelteverker, Norway
  Particle size in the range of 70–350 μm.
Copper oxide:
  Prepared according to U.S. Pat. No. 5,306,328, Example 5.
  All other catalysts and activators used are commercially available from Fluka Chemie GmbH, Germany.
Experimental plant:
  Laboratory fluidized-bed reactor (vertical glass tube having an internal diameter of 25 mm and a height of 500 mm) provided with heating tape, gas distribution frit, distillation head with brine cooling and receiver flask.
Standardized procedure:
  Start-up phase: 120 g of silicon are intimately mixed with the catalysts, placed in the reactor and heated to 340° C. under a nitrogen stream of 40 l/h.
  40 l/h of methyl chloride together with the appropriate activators are passed through the reactor and the catalyst composition is heated to 395° C. After an induction time in the range of 20–30 minutes, silane formation commences (start time), the reaction temperature is reduced to 360° C. and 50 ml of methylchlorosilane are collected.
Production phase:
  Subsequently, a further 30 ml of methylchlorosilanes are collected. The time for forming this 30 ml of silanes is referred to as the production phase, the production rate (PR2) is calculated according to the formula $$PR2 = \frac{\text{mg of methylchlorosilanes} - \text{mg of activators metered in}}{\text{surface area of the silicon} \times \text{minutes}}$$

The silane composition of the 30 ml of methylchlorosilanes was determined in percent by weight by means of GC analysis.

Comparative Examples 1–6 without activator (not according to the invention):

Proof is obtained that the productivity depends very strongly on the chemical form of the catalyst. The catalyst components used are shown in g in Table 1.

TABLE I

| Ex. | $CuO_{0.9}$ | CuCl | Zn | $ZnCl_2$ | ZnO | Sn | Sb |
|---|---|---|---|---|---|---|---|
| 1 | 6.00 | | | | 1.00 | 0.008 | |
| 2 | 6.00 | | | | 1.00 | | 0.006 |
| 3 | 6.00 | | | 1.67 | | 0.008 | |
| 4 | 6.00 | | 0.81 | | | 0.008 | |
| 5 | | 7.48 | | 1.67 | 1.00 | 0.008 | |
| 6 | 6.00 | | | | | | 0.006 |

Table II shows the results from the Comparative Examples 1–6. The production rate (PR2) is given in mg of silane/m²·min. The concentrations of $Me_2SiCl_2$ in the crude silane and the concentration of $Me_2SiCl_2$ in the crude silane standardized to 0% by weight of $HSiMeCl_2$ (A) are given in percent by weight. In Example 4, the production phase was not reached within a reaction time of 3 hours.

TABLE II

| Examples | PR2 | % $Me_2SiCl_2$ | A |
|---|---|---|---|
| 1 | 100.1 | 87.9 | 89.1 |
| 2 | 104.2 | 82.3 | 83.2 |
| 3 | 141.8 | 78.0 | 81.5 |
| 4 | 0.0 | — | — |
| 5 | 134.8 | 84.3 | 86.0 |
| 6 | 107.2 | 77.0 | 79.0 |

Comparative Example 7 (not according to the invention):

Proof is obtained that when using t-butyl chloride, a model substance for activation using t-alkyl halides, the activating action is lower than with the activators of the invention, and that undesired new silanes and also unreacted t-butyl chloride are present in the crude silane.

| Catalysts | 6.00 g | $CuO_{0.9}$ |
|---|---|---|
| | 1.00 g | ZnO |
| | 0.008 g | Sn |

Activator:

0.30 l/h of t-butyl chloride (gaseous) blown in with the methyl chloride during the entire course of the reaction.
PR2: 133.5
$Me_2SiCl_2$: 82.4%

The $^1$H-NMR spectrum of the crude silane showed about 1% of t-butylsilanes and also t-butyl chloride.

Examples 1–4

| Catalysts: | 6.00 g | $CuO_{0.9}$ |
|---|---|---|
| | 1.00 g | ZnO |
| | 0.008 g | Sn |

Activator:

Methyldichlorosilane blown in with the methyl chloride during the entire course of the reaction.

(A=% by weight of $Me_2SiCl_2$ in the crude silane, standardized to 0% of $HMeSiCl_2$).

TABLE III

| Example | l/h $HMeSiCl_2$, gaseous | PR2 | % by weight of $Me_2SiCl_2$ | A |
|---|---|---|---|---|
| 1 | 0.33 | 151.7 | 85.4 | 90.0 |
| 2 | 0.50 | 156.4 | 82.1 | 89.9 |
| 3 | 0.75 | 153.6 | 76.1 | 86.7 |
| 4 | 1.10 | 154.4 | 74.0 | 85.3 |

Examples 5–7

The procedure of Example 1 was repeated except that the metering in of $HMeSiCl_2$ was stopped as soon as R ml of crude silane had formed and the reaction was subsequently continued using pure methyl chloride.

TABLE IV

| Example | R[ml] | PR2 | % by weight of $Me_2SiCl_2$ | A |
|---|---|---|---|---|
| 5 | 2 | 149.6 | 87.0 | 89.4 |
| 6 | 10 | 154.7 | 85.9 | 87.4 |
| 7 | 0.05 | 148.6 | 84.1 | 86.0 |

Examples 8–9

The procedure of Example 1 was repeated except that 1,1,2,2-tetramethyldichlorosilane was used as activator.

TABLE V

| Example | l/h $(Me_2ClSi)_2$, gaseous | PR2 | % by weight of $Me_2SiCl_2$ | A |
|---|---|---|---|---|
| 8 | 0.34 | 136.8 | 82.9 | 83.7 |
| 9 | 0.43 | 136.0 | 81.4 | 82.2 |

Example 10

Catalysts: 6.00 g $CuO_{0.9}$
1.67 g $ZnCl_2$
0.008 g Sn

Activator:

0.35 l/h of gaseous methyldichlorosilane were blown into the reactor together with the methyl chloride during the entire course of the reaction.

PR2=147.5; % by weight of $Me_2SiCl$=76.9%

% by weight of $Me_2SiCl_2$ standardized to 0% of $HMeSiCl_2$=81.1%

Example 11

| Catalysts: | 6.00 g | $CuO_{0.9}$ |
|---|---|---|
| | 1.00 g | ZnO |
| | 0.006 g | Sb |

Activator:

0.59 l/h of gaseous methyldichlorosilane were blown into the reactor together with the methyl chloride during the entire course of the reaction.

PR2=138.4; % by weight of $Me_2SiCl_2$=63.7%

% by weight of $Me_2SiCl_2$ standardized to 0% of $HMeSiCl_2$=78.2%

Examples 12–16

Catalyst and activator are shown in Table VI

TABLE VI

| Example | CuO 0.9 g | CuCl g | ZnO g | Zn g | Sb g | Sn g | l/h $HSiCl_3$ | l/h $HMeSiCl_2$ | l/h $Me_2SiCl_2$ |
|---|---|---|---|---|---|---|---|---|---|
| 12 | 6.00 | | 1.00 | | | 0.008 | 0.88 | | |
| 13 | 6.00 | | 1.00 | | 0.006 | | | 0.72 | |
| 14 | 6.00 | | | 0.81 | | 0.008 | | | 0.51 |
| 15 | 6.00 | | | 0.81 | | 0.008 | 1.01 | | |
| 16 | | 7.48 | 1.00 | | | 0.008 | | 1.52 | |

The metering in or activator was stopped as soon as 10 ml of crude silane had formed. The reaction was ubsequently continued using pure methyl chloride. The results are shown in Table VII.

TABLE VII

| Example | PR2 | % by weight of $Me_2SiCl_2$ | A |
|---|---|---|---|
| 12 | 149.0 | 85.3 | 87.0 |
| 13 | 176.6 | 82.6 | 84.7 |
| 14 | 136.3 | 86.9 | 88.2 |
| 15 | 165.1 | 88.4 | 89.7 |
| 16 | 256.4 | 84.1 | 87.1 |

Example 17

| Catalysts: | 6.00 g | $CuO_{0.9}$ |
|---|---|---|
| | 0.81 g | Zn |
| | 0.008 g | Sn |

Activator:

0.45 l/h of gaseous dimethyldichlorosilane was blown into the reactor together with the methyl chloride during the entire course of the reaction.

PR2=120.5; % by weight of $Me_2SiCl_2$=88.1%

% by weight of $Me_2SiCl_2$ standardized to 0% of $HMeSiCl_2$=89.1%

Example 18

| Catalysts: | 6.00 g | $CuO_{0.9}$ |
|---|---|---|
| | 1.67 g | $ZnCl_2$ |
| | 0.006 g | Sb |

Activator:

0.53 l/h of gaseous methyldichlorosilane was blown into the reactor together with the methyl chloride during the entire course of the reaction.

PR2=134.4; % by weight of $Me_2SiCl_2$=75.5%

% by weight of $Me_2SiCl_2$ standardized to 0% of $HMeSiCl_2$=80.1%

Example 19, Comparative Example 8

Silicon: Elkem Silgrain from Elkem, Norway particle size in the range of 70–250 μm

| Catalysts: | 6.00 g | $CuO_{0.9}$ |
|---|---|---|
| | 1.00 g | ZnO |
| | 0.008 g | Sn |

Activator:

In the Comparative Example 8, no activator was added; in Example 19, 0.58 l/h of gaseous methyldichlorosilane was added to the methyl chloride until 10 ml of crude silane had formed. The reaction was subsequently continued using pure methyl chloride.

TABLE VIII

| | PR2 | % by weight of $Me_2SiCl_2$ | A |
|---|---|---|---|
| Comparative Example 8 | 68.4 | 85.9 | 86.8 |
| Example 19 | 100.5 | 87.0 | 88.4 |

Examples 20–22

| Catalysts: | 6.00 g | $CuO_{0.9}$ |
|---|---|---|
| | 1.00 g | ZnO |
| | 0.008 g | Sn |

Activator:

Dimethyldichlorosilane blown into the reactor together with methyl chloride during the entire course of the reaction.

TABLE IX

| Example | l/h $Me_2SiCl_2$, gaseous | PR2 | % by weight of $Me_2SiCl_2$ |
|---|---|---|---|
| 20 | 0.21 | 135.2 | 88.1 |
| 21 | 0.35 | 139.0 | 90.1 |
| 22 | 0.47 | 141.4 | 91.3 |

Example 23

| Catalysts: | 6.00 g | $CuO_{0.9}$ |
|---|---|---|
| | 1.00 g | ZnO |
| | 0.008 g | Sn |

Activator:

0.30 l/h of gaseous trimethylchlorosilane was blown into the reactor together with the methyl chloride during the entire course of the reaction.

PR2=135.5; % by weight of $Me_2SiCl_2$=86.9%

What is claimed is:

1. A process for preparing dimethyldichlorosilane by reacting chloromethane with silicon in the presence of a catalyst combination of the metals or components of the metals
   a) copper,
   b) zinc and
   c) tin and/or antimony, and
activators selected from the group consisting of chlorosilanes of the formula $$(H_3C)_aSiH_bCl_c \qquad (I),$$

where
   a and b are, independently of one another, 0, 1, 2 or 3 and
   c is 1, 2, 3 or 4, and chlorodisilanes of the formula $$(H_3C)_dHeCl_fSi\text{—}Si(H_3C)_gH_hCl_i \qquad (II),$$

where
   d and e are, independently of one another, 0, 1 or 2,
   f is 1, 2 or 3 and
   g, h and i are, independently of one another, 0, 1, 2 or 3,
where the activators are added in gaseous form containing at most 15% by volume of hydrogen.

2. The process as claimed in claim 1, wherein the gas fed into the reactor contains at least 0.05% by volume of activator, calculated as gaseous activator.

3. The process as claimed in claim 1, wherein from 0.5% to 10% by weight of copper catalyst, based on metallic copper and silicon is present.

4. The process as claimed in claim 1, wherein from 0.5% to 60% by weight of Zn, based on copper, is present.

5. The process as claimed in claim 1, wherein from 200 to 8000 ppm of antimony and/or tin, based on the copper is present.

6. The process as claimed in claim 1, wherein the activators are selected from the group consisting of methyltrichlorosilane, methyldichlorosilane and dimethyldichlorosilane.

* * * * *